US009357912B2

(12) United States Patent
Zhang

(10) Patent No.: US 9,357,912 B2
(45) Date of Patent: Jun. 7, 2016

(54) APPARATUS AND METHOD FOR CHARACTERIZING BIOMECHANICAL PROPERTIES OF EYE TISSUE

(71) Applicant: Yan Zhang, Vernon, CT (US)

(72) Inventor: Yan Zhang, Vernon, CT (US)

(*) Notice: Subject to any disclaimer, the term of this patent is extended or adjusted under 35 U.S.C. 154(b) by 373 days.

(21) Appl. No.: 14/020,944

(22) Filed: Sep. 9, 2013

(65) Prior Publication Data

US 2015/0070651 A1 Mar. 12, 2015

(51) Int. Cl.
*A61B 3/14* (2006.01)
*A61B 3/00* (2006.01)
*A61B 3/10* (2006.01)
*A61B 3/02* (2006.01)
*A61B 3/12* (2006.01)

(52) U.S. Cl.
CPC .............. *A61B 3/0025* (2013.01); *A61B 3/1241* (2013.01); *A61B 3/145* (2013.01)

(58) Field of Classification Search
CPC ........ A61B 3/14; A61B 3/103; A61B 3/1015; A61B 3/113; A61B 3/1208; A61B 3/1225; A61B 3/024
USPC ......... 351/206, 200, 205, 210, 218, 221, 222, 351/246
See application file for complete search history.

(56) References Cited

U.S. PATENT DOCUMENTS

| | | | |
|---|---|---|---|
| 4,281,662 A | 8/1981 | Brent | |
| 5,321,501 A | 6/1994 | Fujimoto et al. | |
| 5,459,570 A | 10/1995 | Fujimoto et al. | |
| 5,777,719 A | 7/1998 | Williams | |
| 5,810,005 A * | 9/1998 | Dublin, Jr. ............. | A61B 5/021 600/398 |
| 6,110,110 A | 8/2000 | Dublin et al. | |
| 7,935,058 B2 | 5/2011 | Dupps et al. | |
| 8,613,710 B2 * | 12/2013 | Kolanko ................ | A61B 5/021 351/200 |
| 2006/0194874 A1* | 8/2006 | Menotti ............... | A61K 31/225 514/546 |
| 2008/0088795 A1* | 4/2008 | Goldstein .............. | A61B 3/117 351/206 |
| 2011/0237999 A1 | 9/2011 | Muller et al. | |

OTHER PUBLICATIONS

Patton, Retinal image analysis: Concepts, applications and potential, Progress in Retinal and Eye Research, 2006, 99-127, 25, Elsevier Inc., USA.
Hollman, Three-Dimensional Mapping of Strain in Ex Vivo Porcine Cornea with an Ultrasound Elasticity Microscope, 33rd Annual International Conference of the IEEE EMBS, USA.
Downs, Biomechanics of the Optic Nerve Head, 2010, 183-201, Elsevier Inc., USA.
Amundsen, Noninvasive Myocardial Strain Measurement by Speckle Tracking Echocardiography, Journal of the American College of Cardiology, 2006, 789-793, 47, 4, Elsevier, USA.
Korinek, Two-dimensional Strain—A Doppler-Independent Ultrasound Method for Quantitation of Regional Deformation: Validation In Vitro and In Vivo, Journal of the American.

(Continued)

*Primary Examiner* — Dawayne A Pinkney
(74) *Attorney, Agent, or Firm* — UConn IP Law Clinic; Melanie Raubeson; Susan K. Pocchiari

(57) ABSTRACT

The present invention relates generally to apparatus and methods for evaluating the condition and properties of eye tissue. More particularly, the present invention is directed to apparatus and methods for non-invasively characterizing the biomechanical properties of eye tissue by utilizing an internal perturbation component.

15 Claims, 6 Drawing Sheets

(56) References Cited

OTHER PUBLICATIONS

Society of Echocardiography, 2005, 1247-1253, 18, 12, Elsevier Inc., USA.

Reant, Experimental Validation of Circumferential, Longitudinal and Radial 2-Dimenstional Strain During Dobutamine Stress Echocardiography in Ischemic Conditions, Journal of the American College of Cardiology, 2008, 149-157, 51, 2, Elsevier Inc., USA.

* cited by examiner

APPARATUS AND METHOD FOR CHARACTERIZING BIOMECHANICAL PROPERTIES OF EYE TISSUE

TECHNICAL FIELD

The present invention is directed generally to apparatus and methods for evaluating the condition and properties of eye tissue. More particularly, the present invention is directed to apparatus and methods for non-invasively characterizing the biomechanical properties of eye tissue.

BACKGROUND OF THE INVENTION

The eye comprises cells and tissues that vary in elasticity. Variations in the biomechanical properties of ocular tissue, including elasticity and strain, may be attributed to the presence of prevalent diseases, such as diabetes and high blood pressure. Therefore, the characterization of these properties plays a critical role in monitoring the normal function and the pathophysiology of the eye.

Current screening tools to measure variations of ocular biomechanical properties require the use of mechanical forces, such as pressing, stretching, or shearing a sample, followed by a measurement of the response. These tools are impractical for use in vivo as they require the removal of the sample from the body. Other tools for measuring these properties consist of an external and invasive perturbation component that introduces stress to the eye prior to measurement of its properties.

It is desirable that a screening tool utilize non-invasive imaging for measuring the biomechanical properties of eye tissue by employing an internal perturbation component. It is further desirable that the screening tool characterizes these properties in the absence of mechanical forces.

From the above, it is therefore apparent that there exists a need in the art to overcome the deficiencies and limitations described herein and above.

SUMMARY OF THE INVENTION

Disclosed herein is an apparatus for characterizing biomechanical properties of eye tissue comprising a light source that illuminates a subject's eye tissue with a beam of light, wherein the beam of light is reflected from the eye tissue, and wherein the reflected light carries an image of the eye tissue; a lens through which the reflected light passes; one or more imaging pathways that focus the image(s) from one or more viewing angles; one or more detectors which detect the image (s) and generate image output(s); a measurement device that measures the subject's blood pressure; and a computer processor that compares an image captured during the subject's systolic phase (i.e., systole) to an image captured during the subject's diastolic phase (i.e., diastole), and wherein the computer processor calculates the strain in the eye tissue. In one embodiment, the apparatus further comprises a beam splitter which reflects the beam of light from the light source onto the subject's eye tissue.

The invention encompasses related methods to measure biomechanical properties of eye tissue using the disclosed apparatus comprising: illuminating a subject's eye tissue with a beam of light either directly from a light source or indirectly through a lens or reflected from a beam splitter, wherein the beam of light is reflected from the eye tissue, and wherein the reflected light carries an image of the eye tissue; focusing the reflected light using a lens; focusing the image through an imaging pathway; detecting the image; transmitting an image output to a computer processor; measuring the subject's blood pressure; and analyzing the image output captured during the systolic phase of the subject's blood pressure and the image output captured during the diastolic phase of the subject's blood pressure to determine the amount of strain in the eye tissue.

In one embodiment, the method comprises illuminating a subject's eye tissue with a beam of light either directly from a light source or indirectly through a lens or reflected from a beam splitter, wherein the beam of light is reflected from the eye tissue, and wherein the reflected light carries an image of the eye tissue; focusing the reflected light using a lens; focusing a first image through a first imaging pathway from a first viewing angle; focusing a second image through a second imaging pathway from a second viewing angle; detecting the first image using a first detector; transmitting a first image output to a computer processor; detecting the second image using a second detector; transmitting a second image output to the computer processor; measuring the subject's blood pressure; and analyzing via the computer processor the image output captured during the systolic phase of the subject's blood pressure and the image output captured during the diastolic phase of the subject's blood pressure to determine the amount of strain in the eye tissue.

In one embodiment, the retina is illuminated with a light beam. In another embodiment, the apparatus and method are used to measure strain in ocular blood vessels, including but not limited to the retinal blood vessels. The apparatus and methods may further comprise a trigger mechanism wherein the subject's heartbeat signals the detector(s) to begin detecting images.

DETAILED DESCRIPTION OF INVENTION

Figure 1:
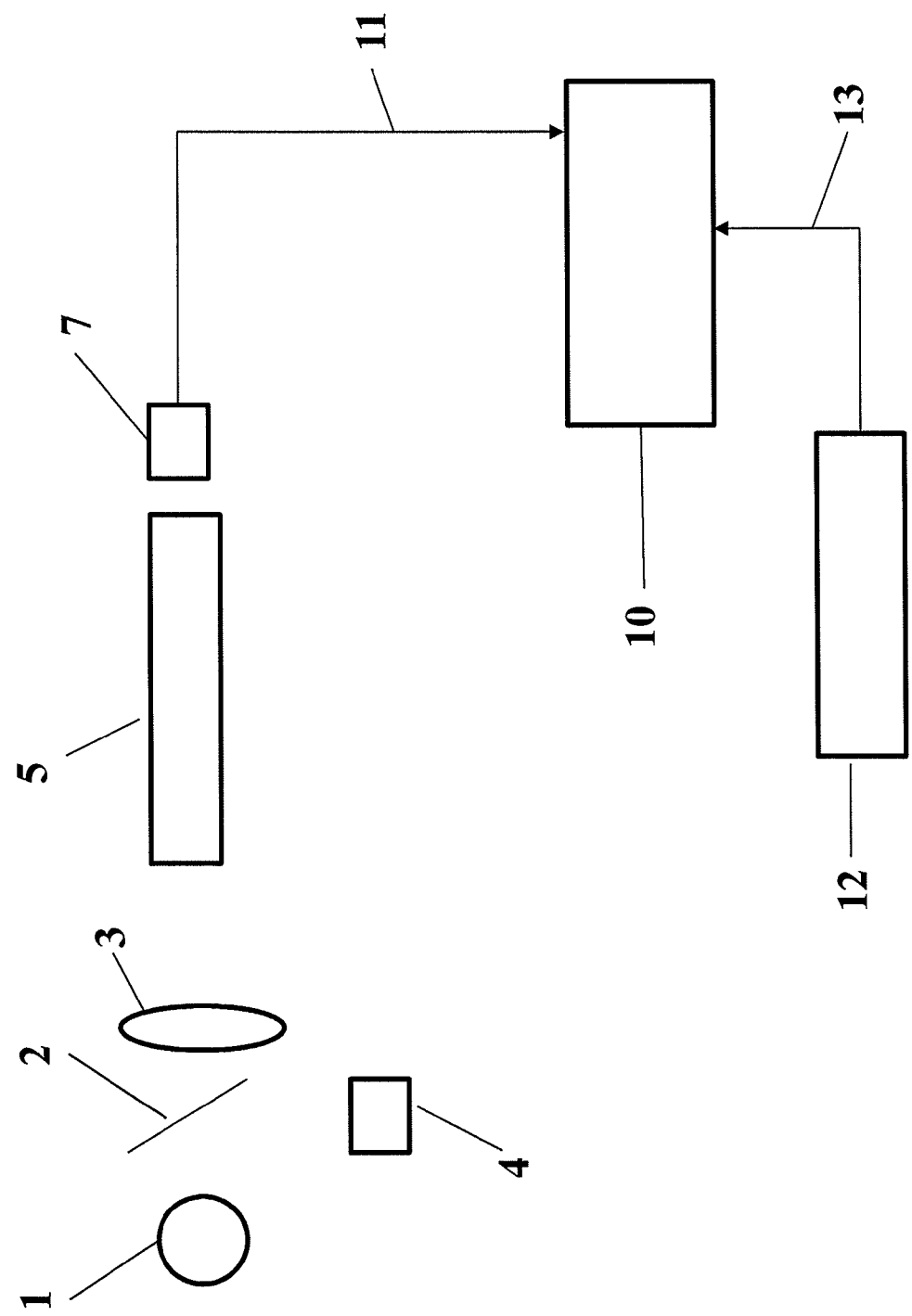
FIG. 1 illustrates an embodiment of the apparatus in free running frame acquisition mode comprising a single imaging pathway and a single detector.

Detailed embodiments of the present invention are disclosed herein. However, it will be readily apparent to those skilled in the art that the disclosed embodiments are merely exemplary of the invention, which may be embodied in various forms, modifications, and equivalent arrangements without departing from the substance or scope of the present invention, the figures are not necessarily to scale, and some features may be exaggerated to show details of particular components or steps. The invention both as to organization and method of practice, together with the further objects and advantages thereof, may best be understood by reference to the following description taken in connection with the accompanying drawings.

The present invention pertains to apparatus and methods of use thereof for non-invasive characterization of the biomechanical properties of eye tissue. The apparatus comprises a light source, optionally, a beam splitter, a lens, one or more imaging pathways, one or more detectors, a device capable of measuring blood pressure and heartbeat, and a processor for comparing images and calculating blood vessel strain. In an embodiment, the apparatus further comprises a trigger mechanism which signals the detector(s) to begin detecting images.

Strain and blood pressure (i.e., stress) can be used as an indication of the health of the blood vessels. When the light illuminates the subject's eye tissue, the eye tissue is masked by a multitude of bright spots known as a "speckle pattern." The detector(s) capture multiple images over a period of several milliseconds, approximately one heartbeat at a time. One of the images is captured during the subject's systolic phase while another image is captured during the subject's diastolic phase. Strain causes a shift in the speckle pattern. Thus, strain can be calculated by comparing an image during systole to an image during diastole. As used herein, "during systole" and "during diastole" refers to "at" or "near" the respective event. For example, at systolic pressure or at a point before or after peak systolic pressure, including but not limited to within about 1% of peak, 5% of peak, 10% of peak, or 20% of peak. Further, an indication of the health of the blood vessels can be calculated using the formula: HI=A/B, where "HI" is the health indicator, "A" is the mean strain number, and "B" is the difference between systolic and diastolic pressures (i.e., systole−diastole). In other embodiments, "A" may be defined as the maximum strain number or the average strain number. In other embodiments, "B" may be defined as a percentage of the difference between the systolic pressure and the diastolic pressure, including but not limited to about 50%, about 60%, about 70%, about 80%, about 90%, and about 95%. A large HI number indicates a softer blood vessel compared to one having a smaller HI number.

The term "light" refers broadly to electromagnetic radiation of any frequency, including infrared, visible, ultraviolet, and X-ray.

Referring to an embodiment of the invention as shown in FIG. 1, the invention provides an apparatus for characterizing biomechanical properties of eye tissue comprising a beam splitter 2, a lens 3, a light source 4, an imaging pathway 5, a detector 7, an image output 11, a measurement device 12, an electrical signal output 13, and a computer processor 10. Any appropriate type of optical beam splitter 2 may be used, including but not limited to, a polarizing or nonpolarizing cube, pellicle, or thin plate. Any appropriate type of lens 3 can be used, for example, biconvex and converging, plano-convex, plano-concave, or biconcave and diverging. The light source 4 can be any appropriate device, including but not limited to, semiconductors such as superluminescent diodes or light emitting diodes, an electric flash-lamp equipped with or without a color filter, a laser, or a laser connected to a multi-mode optical fiber or a hollow light guide. The imaging pathway 5 may comprise a single lens, multiple lenses, a fiber, a fiber bundle, a mirror, multiple mirrors, or any combination thereof. The detector 7 may comprise any appropriate device capable of capturing an image, for example, a charge-coupled camera or a complementary metal oxide semiconductor. The detector 7 can capture images continuously and can generate an output image 11. The image output 11 may be still or video images. The measurement device 12 is capable of assessing the vital statistics of the subject, including heartbeat, systolic blood pressure and diastolic blood pressure, and generating an electrical signal output 13. The computer processor 10 is capable of analyzing the image output 11 captured during systole and the image output 11 captured during diastole and determining the amount of strain in the eye tissue 1. The computer processor 10 calculates the strain in the eye tissue 1 by generating displacement measurements from the comparison of the captured images. One or more biomechanical properties of the eye tissue can be calculated from the displacement measurement values, for example, stress-strain curves.

Also referring to FIG. 1, a method of the invention comprises: illuminating a beam splitter 2 with a light beam from a light source 4, wherein the light beam is reflected from the beam splitter 2 onto a subject's eye tissue 1, and wherein the light beam is reflected from the subject's eye tissue 1 through a lens 4, focusing an image through an imaging pathway 5, detecting the image with the detector 7, wherein the detector 7 generates an output image 11; measuring the subject's systolic pressure and diastolic pressure using the measurement device 12, analyzing the image output 11 captured during systole and the image output 11 captured during diastole using the computer processor 10, and determining the amount of strain in the eye tissue 1 using the computer processor 10.

Figure 2:
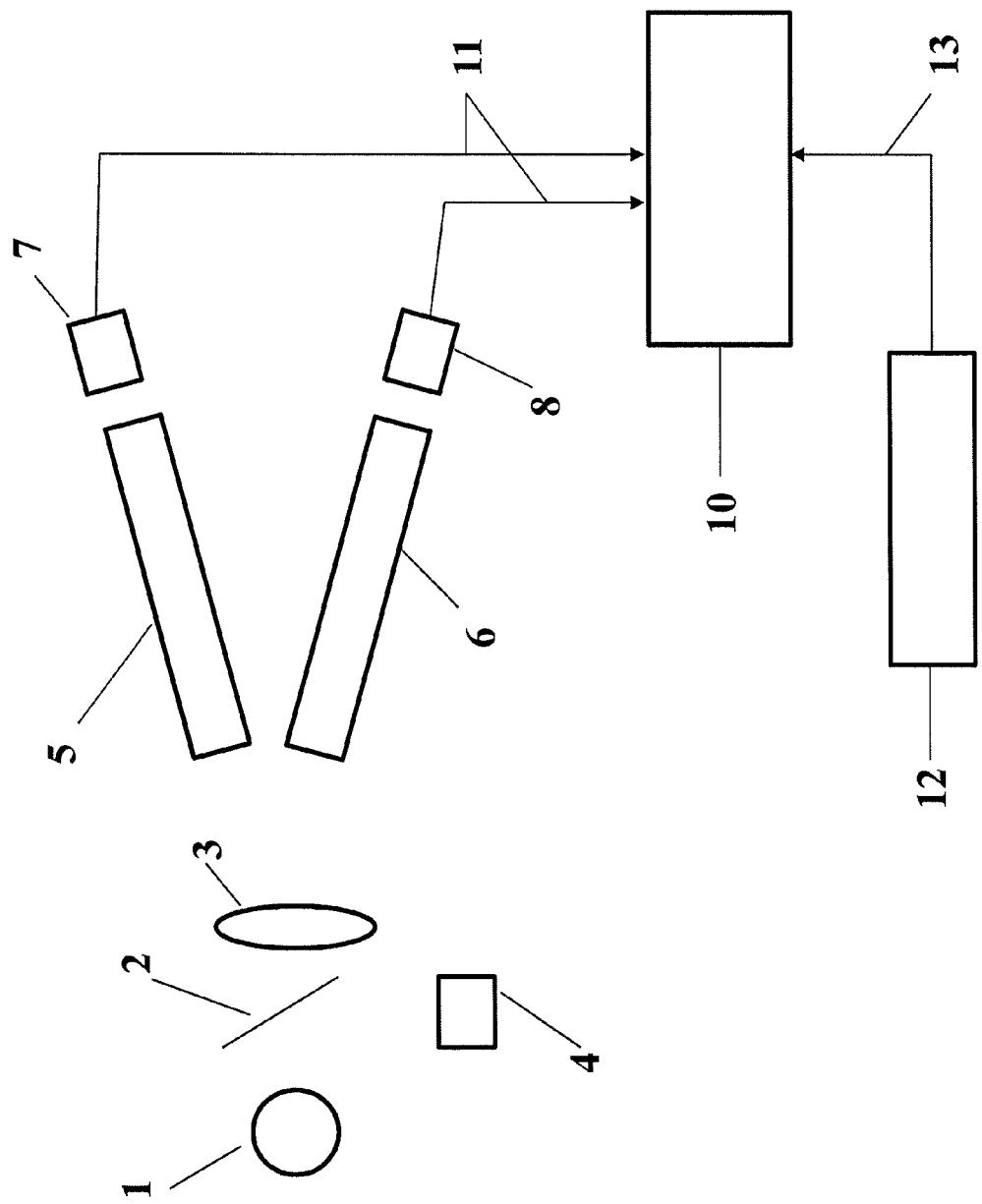
FIG. 2 illustrates an embodiment of the apparatus in free running frame acquisition mode comprising two imaging pathways and two detectors in two viewing angles.

Referring to an embodiment of the invention as shown in FIG. 2, the invention provides an apparatus for characterizing biomechanical properties of eye tissue comprising a beam splitter 2, a lens 3, a light source 4, an imaging pathway 5, a second imaging pathway 6, a detector 7, a second detector 8, an image output 11, a measurement device 12, an electrical signal output 13, and a computer processor 10. The imaging pathway 6 may comprise a single lens, multiple lenses, a fiber, a fiber bundle, a mirror, multiple mirrors, or any combination thereof. The imaging pathway 5 and the imaging pathway 6 may include the same elements and/or configurations or may include different elements and/or configurations. The detector 8 may comprise any appropriate device capable of capturing an image, for example, a charge-coupled camera or a complementary metal oxide semiconductor. The detector 8 can capture images continuously and can generate an output image 11. The detector 7 and the detector 8 may be the same type of detecting device or may be different types of detecting devices.

Also referring to FIG. 2, a method of the invention comprises: illuminating a beam splitter 2 with a light beam from a light source 4, wherein the light beam is reflected from the beam splitter 2 onto a subject's eye tissue 1, and wherein the light beam is reflected from the subject's eye tissue 1 through a lens 4, focusing a first image through a first imaging pathway 5, detecting the first image with a first detector 7, wherein the first detector 7 generates an image output 11, focusing a second image through a second imaging pathway 6, detecting the second image with a second detector 8, wherein the second detector 8 generates an image output 11, measuring the subject's systolic pressure and diastolic pressure using the measurement device 12, analyzing the image output 11 captured during systole and the image output 11 captured during diastole using the computer processor 10, and determining the amount of strain in the eye tissue 1 using the computer processor 10.

In another embodiment, computer processor 10 further calculates the ratio of strain to the difference between the systolic and diastolic pressures.

In another embodiment, computer processor 10 further calculates a distribution of the ratio of the stress to the strain of the eye tissue.

Figure 3:
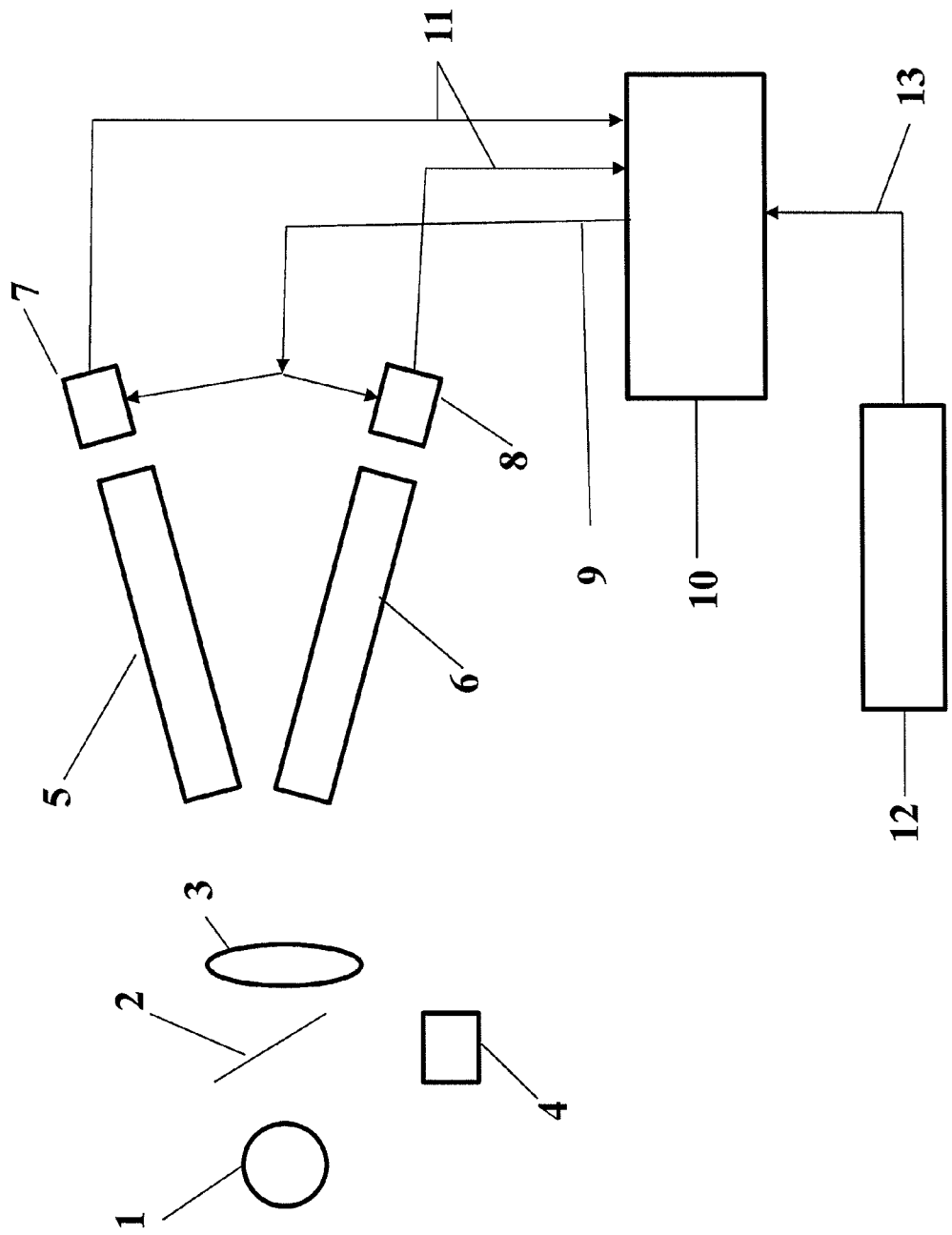
FIG. 3 illustrates an embodiment of the apparatus in trigger mode comprising two imaging pathways and two detectors in two viewing angles.

In another embodiment illustrated in FIG. 3, in addition to the elements illustrated in FIG. 2, the embodiment further includes a trigger signal 9 which signals the computer processor 10 to trigger detectors 7 and 8 to capture a series of images corresponding to the subject's heartbeat. The embodiment illustrated in FIG. 1 may also include a trigger signal 9. The trigger signal 9 may be initiated by the subject's vital statistics, including but not limited to heartbeat, systolic blood pressure, and diastolic blood pressure.

In one embodiment, the method comprises capturing a series of images over a span of a plurality of heartbeats and analyzing the tissue strain changes during this period.

In another embodiment, the retina is illuminated with a light beam. In another embodiment, the apparatus and method are used to measure the strain in ocular blood vessels, including but not limited to the retinal blood vessels.

It is understood by one skilled in the art that the embodiment comprising two imaging pathways and two detectors which capture beams of light from different viewing angles (e.g., FIGS. 2 and 3) produces a three-dimensional map whereas the embodiment comprising a single imaging pathway and single detector which captures a beam of light from a single viewing angle (e.g., FIG. 1) produces a two-dimensional map.

Figure 4:
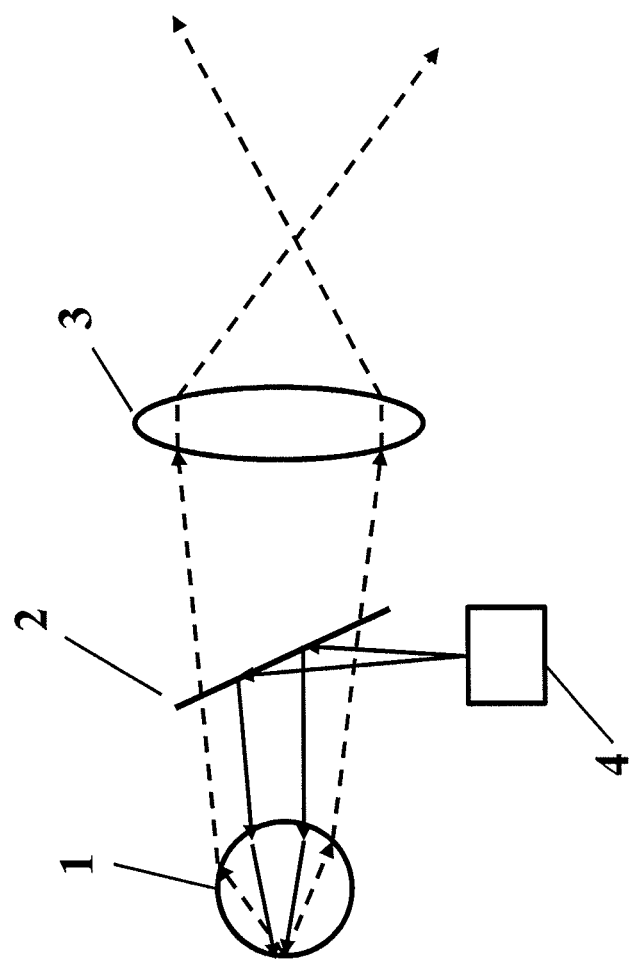
FIG. 4 illustrates an embodiment of the apparatus wherein the light beam is reflected from a beam splitter onto a subject's eye. Solid lines indicate the direction of light rays which are emitted from the light source and reflected from the beam splitter onto the eye. Dashed lines indicate the direction of light rays which are reflected from the eye, through the beam splitter and through the lens.

It will also be understood be one of skill in the art that the presence of a beam splitter is optional. Referring to FIG. 4, the direction of the light beam is shown in an embodiment where the apparatus includes a beam splitter 2. In particular, the light beam is reflected from a beam splitter 2 onto a subject's eye 1. Solid lines indicate the direction of light rays which are emitted from the light source and reflected from the beam splitter 2 onto the eye tissue 1. Dashed lines indicate the direction of light rays which are reflected from the eye tissue 1, through the beam splitter 2 and through a lens 3.

Figure 5:
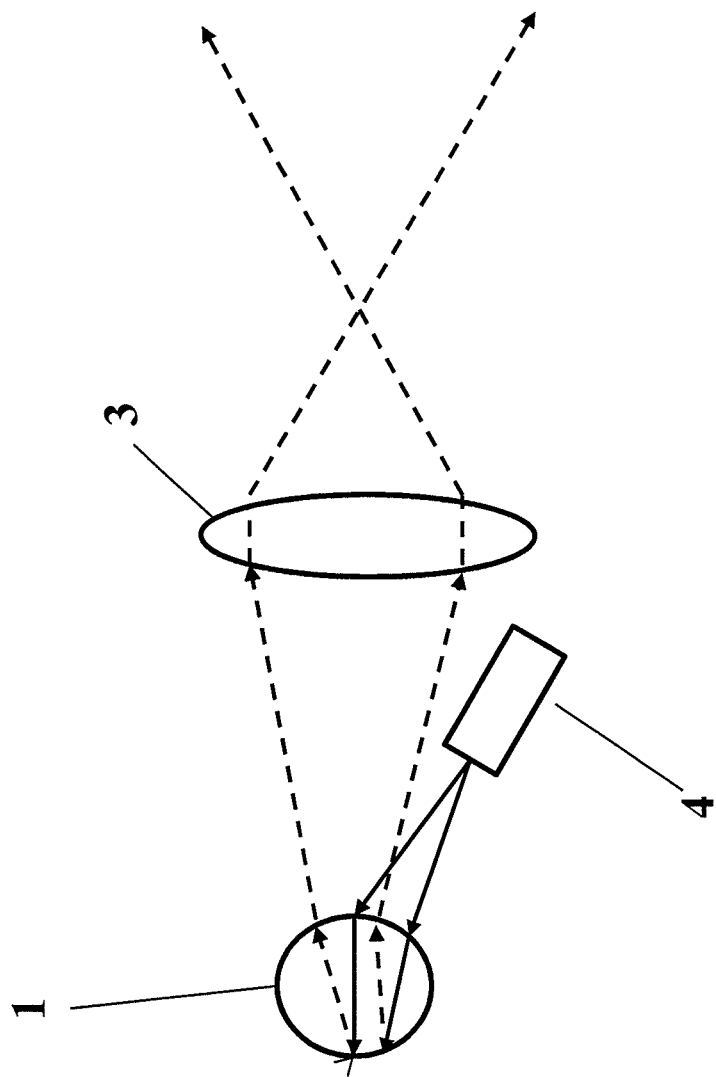
FIG. 5 illustrates an embodiment of the apparatus wherein the light beam illuminates a subject's eye. Solid lines indicate the direction of light rays which are emitted from the light source to the eye. Dashed lines indicate the direction of light rays which are reflected from the eye and through the lens.

Referring to FIG. 5, the direction of the light beam is shown in an embodiment of the apparatus wherein the light beam illuminates a subject's eye tissue 1. Solid lines indicate the direction of light rays which are emitted from the light source 4 to the eye tissue 1. Dashed lines indicate the direction of light rays which are reflected from the eye tissue 1 and through the lens 3.

Figure 6:
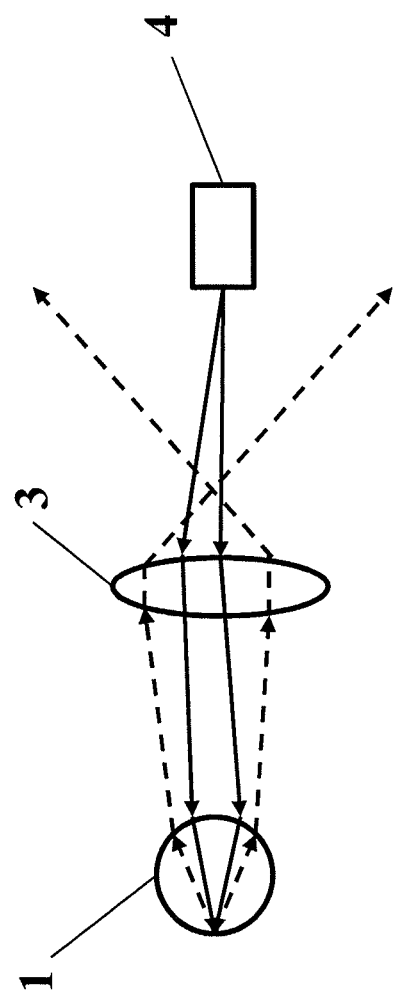
FIG. 6 illustrates an embodiment of the apparatus wherein a light beam illuminates a subject's eye after passing through a lens. Solid lines indicate the direction of light rays which are emitted from the light source and through the lens to illuminate the eye. Dashed lines indicate the direction of light rays which are reflected from the eye and through the lens.

Referring to FIG. 6, the direction of the light beam is shown in another embodiment of the invention wherein a light source 4 emits a light beam which passes through a lens 3 and illuminates a subject's eye tissue 1 (shown in solid lines). The light beam is reflected from the subject's eye tissue 1 and passes through the lens 3 (shown in dashed lines).

What is claimed is:

1. An apparatus for characterizing biomechanical properties of blood vessels in the retina of a subject's eye tissue comprising:
    a light source that transmits a light beam to illuminate the subject's eye tissue, wherein the light beam is reflected from the eye tissue, and wherein the light beam carries an image of blood vessels in the retina of the eye tissue;
    a lens that focuses the reflected light beam;
    a first imaging pathway that focuses a first image from a first viewing angle;
    a first detector that detects the first focused image;
    a second imaging pathway that focuses a second image from a second viewing angle;
    a second detector that detects the second focused image, wherein the first and the second detected focused images produce a three-dimensional map;
    a measurement device that measures the subject's blood pressure; and
    a computer that analyzes a first three-dimensional map of images captured during a systolic phase of the subject and a second three-dimensional map of images captured during a diastolic phase of the subject, and wherein the computer calculates strain of the blood vessels in the retina of the eye tissue from the two three-dimensional maps of images.

2. The apparatus of claim 1, wherein the computer further calculates the ratio of strain to the difference between systolic and diastolic blood pressures.

3. The apparatus of claim 1 further comprising a trigger mechanism.

4. The apparatus of claim 3, wherein the trigger mechanism is an electrical signal output which corresponds to the subject's heartbeat.

5. The apparatus of claim 1 further comprising a beam splitter, wherein the light beam is reflected from the light source onto the subject's eye tissue.

6. The apparatus of claim 3, wherein the trigger mechanism is an electrical signal output which corresponds to the subject's blood pressure.

7. The apparatus of claim 1, further comprising a second light source emitting a second light beam of a different wavelength.

8. A method to measure biomechanical properties of blood vessels in the retina of a subject's eye tissue comprising:
    illuminating the subject's eye tissue with a light beam, wherein the light beam is reflected from the eye tissue, and wherein the light beam carries an image of blood vessels in the retina of the eye tissue;
    focusing the light beam through a lens;
    focusing a first image through a first imaging pathway from a first viewing angle;
    detecting the first focused image;
    focusing a second image through a second imaging pathway from a second viewing angle;
    detecting the second focused image;
    transmitting a first image output to a computer processor;
    transmitting a second image output to a computer processor;
    producing a three-dimensional map from the first and the second focused images;
    measuring the subject's blood pressure;
    analyzing a first three-dimensional map of images captured during a systolic phase of the subject and a second three-dimensional map of images captured during the a diastolic phase of the subject using a computer processor; and determining the amount of strain in the blood vessels in the retina of the eye tissue from the two three-dimensional maps of images using the computer processor.

9. The method of claim 8, wherein the method is initiated by a trigger signal.

10. The method of claim 9, wherein the trigger signal is an electrical output which corresponds to the subject's heartbeat.

11. The method of claim 8, further comprising calculating the ratio of strain to the difference between systolic and diastolic blood pressures.

12. The method of claim 8, wherein the subject's eye tissue is illuminated with a light beam reflected from a beam splitter.

13. The method of claim 8, wherein a series of images is captured during a plurality of heartbeats.

14. The method of claim 8, wherein the image output is a video.

15. The method of claim 9, wherein the trigger mechanism is an electrical signal output which corresponds to the subject's blood pressure.

\* \* \* \* \*